US010520445B2

(12) United States Patent
Nikolajsen et al.

(10) Patent No.: US 10,520,445 B2
(45) Date of Patent: Dec. 31, 2019

(54) SYSTEM FOR AND METHOD OF PERFORMING LASER INDUCED BREAKDOWN SPECTROSCOPY

(71) Applicant: Foss Analytical A/S, Hilleroed (DK)

(72) Inventors: Thomas Nikolajsen, Hilleroed (DK); Allan Kjaergaard Jensen, Hilleroed (DK)

(73) Assignee: Foss Analytical A/S, Hilleroed (DK)

( * ) Notice: Subject to any disclaimer, the term of this patent is extended or adjusted under 35 U.S.C. 154(b) by 0 days.

(21) Appl. No.: 16/075,775

(22) PCT Filed: Mar. 31, 2016

(86) PCT No.: PCT/IB2016/051829
§ 371 (c)(1),
(2) Date: Aug. 6, 2018

(87) PCT Pub. No.: WO2017/168211
PCT Pub. Date: Oct. 5, 2017

(65) Prior Publication Data
US 2019/0041334 A1    Feb. 7, 2019

(51) Int. Cl.
*G01J 3/30* (2006.01)
*G01N 21/71* (2006.01)
(Continued)

(52) U.S. Cl.
CPC ............ *G01N 21/718* (2013.01); *G01J 3/443* (2013.01); *G01N 1/04* (2013.01); *G01N 1/286* (2013.01);
(Continued)

(58) Field of Classification Search
CPC ........ G01N 21/718; G01N 1/04; G01N 1/286; G01N 2001/045; G01N 2021/0339;
(Continued)

(56) References Cited

U.S. PATENT DOCUMENTS

| 5,583,634 A | 12/1996 | Andre et al. |
| 7,692,789 B1 | 4/2010 | Ebinger et al. |

(Continued)

FOREIGN PATENT DOCUMENTS

| EP | 0168374 A2 | 1/1986 |
| WO | WO-2005/106458 A2 | 11/2005 |

OTHER PUBLICATIONS

International Search Report PCT/ISA/210 for International Application No. PCT/IB2016/051829 dated Oct. 31, 2016.
(Continued)

*Primary Examiner* — Tarifur R Chowdhury
*Assistant Examiner* — Jonathon Cook
(74) *Attorney, Agent, or Firm* — Harness, Dickey & Pierce, P.L.C.

(57) ABSTRACT

A Laser Induced Breakdown Spectrocopy (LIBS) system for the analysis of a sample pellet of a consolidated granular material retained in a tubular container may include a laser source configured to emit a pulsed laser beam towards an exposed surface of the sample pellet; and a sample station configured to hold the cylindrical tubular container in one or more orientations to present an exposed surface of the sample pellet towards the pulsed laser beam. The sample station may induce linear movement of the sample pellet along an axis and to expose a portion of the outer side surface of the sample pellet previously constrained through contact with an inner surface of the cylindrical tubular container. The sample station may induce rotational motion of the outer side surface of the sample pellet around the movement axis to present the portion of the outer side surface as the exposed surface.

4 Claims, 2 Drawing Sheets

Figure 1:
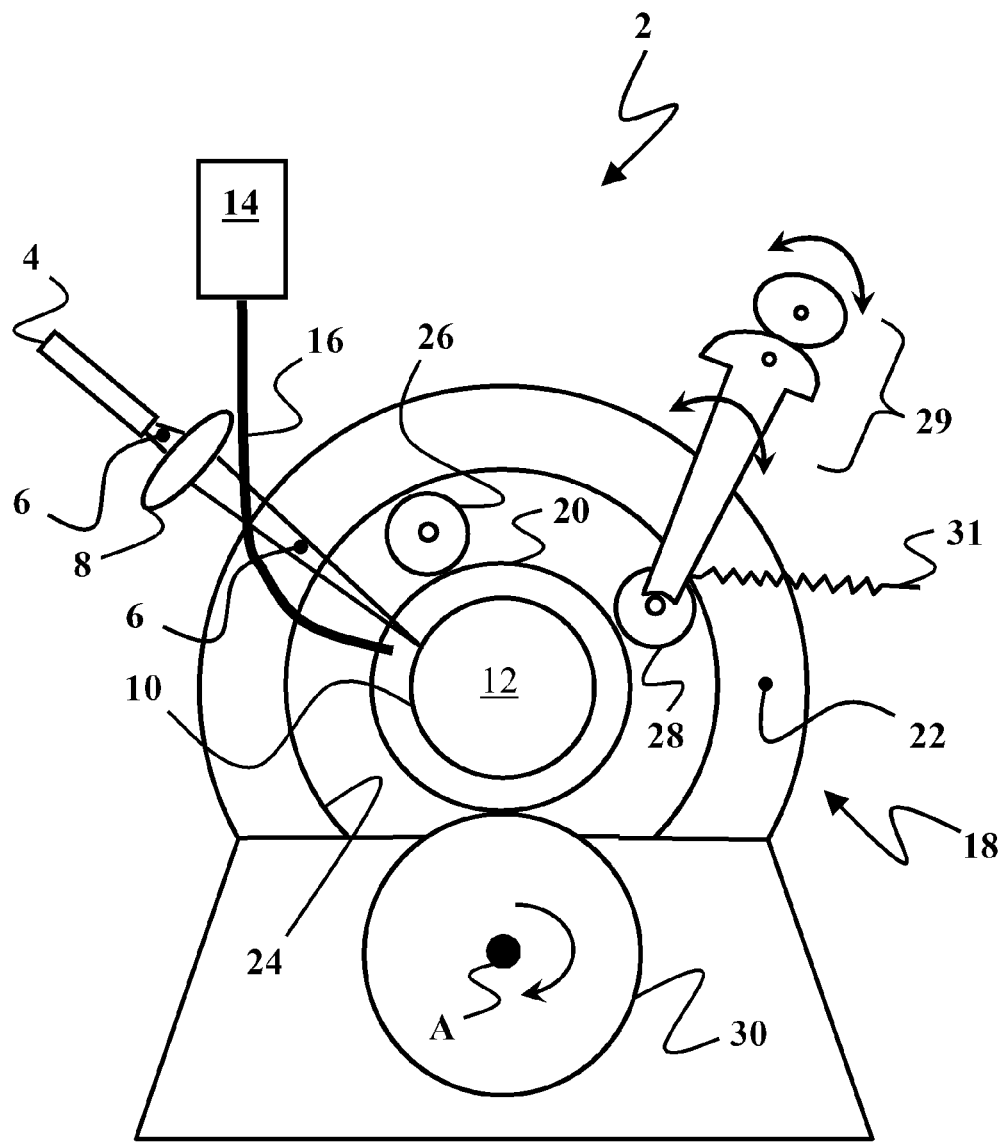

(51) Int. Cl.
*G01J 3/443* (2006.01)
*G01N 1/04* (2006.01)
*G01N 1/28* (2006.01)
*G01N 21/03* (2006.01)

(52) U.S. Cl.
CPC .................. *G01N 2001/045* (2013.01); *G01N 2021/0339* (2013.01)

(58) Field of Classification Search
CPC ..... G01N 2021/5973; G01N 2021/135; G01N 2223/309; G01J 3/443
USPC ........................................................ 356/318
See application file for complete search history.

(56) References Cited

U.S. PATENT DOCUMENTS

| | | |
|---|---|---|
| 2007/0218556 A1 | 9/2007 | Harris et al. |
| 2009/0091740 A1* | 4/2009 | Kane .................. B01L 9/06 356/36 |
| 2013/0271761 A1 | 10/2013 | Rutberg et al. |
| 2016/0018325 A1 | 1/2016 | Elsoee et al. |
| 2016/0069745 A1 | 3/2016 | Wang et al. |

OTHER PUBLICATIONS

Written Opinion of the International Searching Authority PCT/ISA/237 for International Application No. PCT/IB2016/051829 dated Oct. 31, 2016.

* cited by examiner

SYSTEM FOR AND METHOD OF PERFORMING LASER INDUCED BREAKDOWN SPECTROSCOPY

CROSS-REFERENCE TO RELATED APPLICATIONS

This application is a national phase under 35 U.S.C. § 371 of PCT International Application No. PCT/IB2016/051829 which has an International filing date of Mar. 31, 2016, the entire contents of each of which are hereby incorporated by reference.

The present invention relates to a system for and a method of performing Laser Induced Breakdown Spectrocopy (LIBS) and in particular to a system for and a method of performing LIBS analysis of granular samples.

LIBS is a known analysis technique which is employed in the measurement of the concentrations of elemental components of a sample. A high energy density laser pulse is used to generate a plasma at the surface of the sample. The plasma contains a mixture of excited atoms representative of the elemental composition of the sample. As the plasma cools the excited atoms emit optical radiation that is characteristic of the atom emitting it. As the intensity of the characteristic radiation is related to the number of atoms in the plasma and ultimately the number of atoms in the sample then spectrophotometric analysis of the so emitted radiation may be employed to provide information on the concentration of elements present in the sample.

When analysing granular samples it is known, for example from U.S. 2007/0218556, to present the sample for analysis as a single consolidated mass in the form of a pressed pellet. The pellet is made by placing the granular material, that is, material composed of individual or partially agglomerated granules, pieces or particles, for example ground, shredded or pulverised plant or soil material; foodstuff or its intermediate products; or pharmaceutical products; into a cylindrical tubular container and pressing the granular material to consolidate it into the pellet. The pellet in the cylindrical tubular container is then moved into the path of the laser beam for the subsequent LIBS analysis of an exposed upper surface.

A LIBS analyser, such as disclosed for example in U.S. Pat. No. 5,583,634, in U.S. 2007/0218556 or in U.S.2013/0271761, therefore generally comprises a laser source capable of generating a laser beam pulse of typically between 10-500 milliJules (mJ) for the order of 1-10 nanoseconds (ns) at a repetition rate of up to a few tens of hertz; focussing optics for focusing the laser beam at a spot of around 10 micrometers ($\mu$m) diameter on the exposed surface of the sample; collection optics for collecting optical radiation emitted by the plasma and a sample station configured to hold the sample orientated to present the exposed surface at a distance from the focussing optics. The optical radiation collected via the collection optics may then be provided to a spectrometer which generates wavelength dependent intensity data from the so provided optical radiation and supplies the data for analysis to determine the elemental concentration of the sample.

The amount of energy produced by such a laser source may also generate relatively large amounts of black body (or 'continuum') radiation, by means of a general heating of the sample. This radiation acts as a background from which the optical radiation emitted by the plasma must be differentiated. Lower energy laser sources may be employed to overcome this problem. However, the use of a lower energy laser source will increase the necessary precision by which the focussing optics must focus the laser beam at the sample in order to ensure a sufficient energy density at its surface for plasma generation. This is especially a problem when investigating granular samples as the surface of the sample presented for interaction with the laser beam tends to present height variations as measured along the optical axis of the focussing optics. Even pelletized samples may present this problem as it has been found that such samples tent to 'relax' causing uneven expansion of any unconfined, that is to say, exposed, surface. Relatively complicated automatically adjustable focussing optics has been proposed, for example in U.S. 2013/0271761, to maintain the laser beam in focus at the surface as a solution to the problem of surface unevenness.

Additionally, with each plasma formation the laser beam removes a small portion of the surface which creates additional height variations. Eventually a crater is formed which results in the laser beam becoming out of focus in the crater. To mitigate this the sample container is often mounted on a moveable X-Y sample stage and the sample container moved after one or more laser pulses in order to present new portions of the exposed upper surface for LIBS analysis. Movement of the sample stage in the Z direction may also be provided in order to maintain the laser beam in focus at the surface of the sample.

According to a first aspect of the present invention there is provided a Laser Induced Breakdown Spectrocopy (LIBS) system for the analysis of a sample pellet of consolidated granular material retained in a tubular, preferably cylindrical, container, the system comprising a laser source configured to emit a pulsed laser beam towards an exposed surface of the sample pellet; and a sample station configured to hold the tubular container with the sample pellet orientated to present the exposed surface towards the pulsed laser beam; wherein the sample station comprises an actuator configured to slide the sample pellet along a movement axis out of the tubular container and thereby present a portion of an outer surface of the sample pellet previously constrained through contact with an inner surface of the tubular container as the exposed surface.

Thus, by having a system configured to perform LIBS analysis on an outer surface of the sample pellet which was previously constrained by the inner surface of the tubular container relaxation effects are mitigated. This provides an advantage that the focussing of the pulsed laser beam at the exposed surface can be more accurately maintained without the need for complicated adjustments of any focussing optics or of the sample stage.

In some embodiments the sample station further comprises a rotary drive mechanically connectable to the tubular container to impart a rotational motion thereto to present a plurality of portions of the outer surface as the exposed surface. This facilitates the collection of multiple instances of LIBS spectral data whilst also mitigating the effects of cratering.

In some embodiments the moving of the sample pellet out of the tubular container and imparting rotational movement to the container is concerted to provide spiral portions of the outer surface of the sample pellet as the exposed surface. Collection of multiple instances of LIBS spectral data from different portions of the same sample is thereby further facilitated.

According to a second aspect of the present invention there is provided a method of performing LIBS analysis of a sample pellet of a consolidated granular material, preferably employing the system according to the first aspect of the present invention, the method comprising: locating the granular sample pellet at a distance from focussing optics of a LIBS system; directing laser beam pulses from a laser source onto an exposed surface of the granular sample pellet; wherein locating the granular sample pellet comprise locating a tubular container containing the sample pellet with an outer surface of the sample pellet in contact with an inner surface of the tubular container, the method further comprising moving the sample pellet out of the tubular container linearly along a movement axis to provide a portion of the outer surface previously constrained by the inner surface of the tubular container as the exposed surface.

Thus, by measuring on an outer surface of the sample pellet which was previously constrained by the inner surface of the tubular container relaxation effects are mitigated. This provides an advantage that the focussing of the pulsed laser beam at the exposed surface can be more accurately maintained without the need for complicated adjustments of any focussing optics or of the sample stage.

According to a third aspect of the present invention there is provided a sample station useable in the system according to the first aspect of the present invention and with the method according to the second aspect, the sample station configured to hold a sample for LIBS analysis, the sample station comprising an actuator configured to slide the sample pellet along a movement axis out of the tubular container and thereby present a portion of the outer surface of the sample pellet previously constrained by an inner surface of the tubular container as an exposed surface for LIBS analysis.

Figure 2:
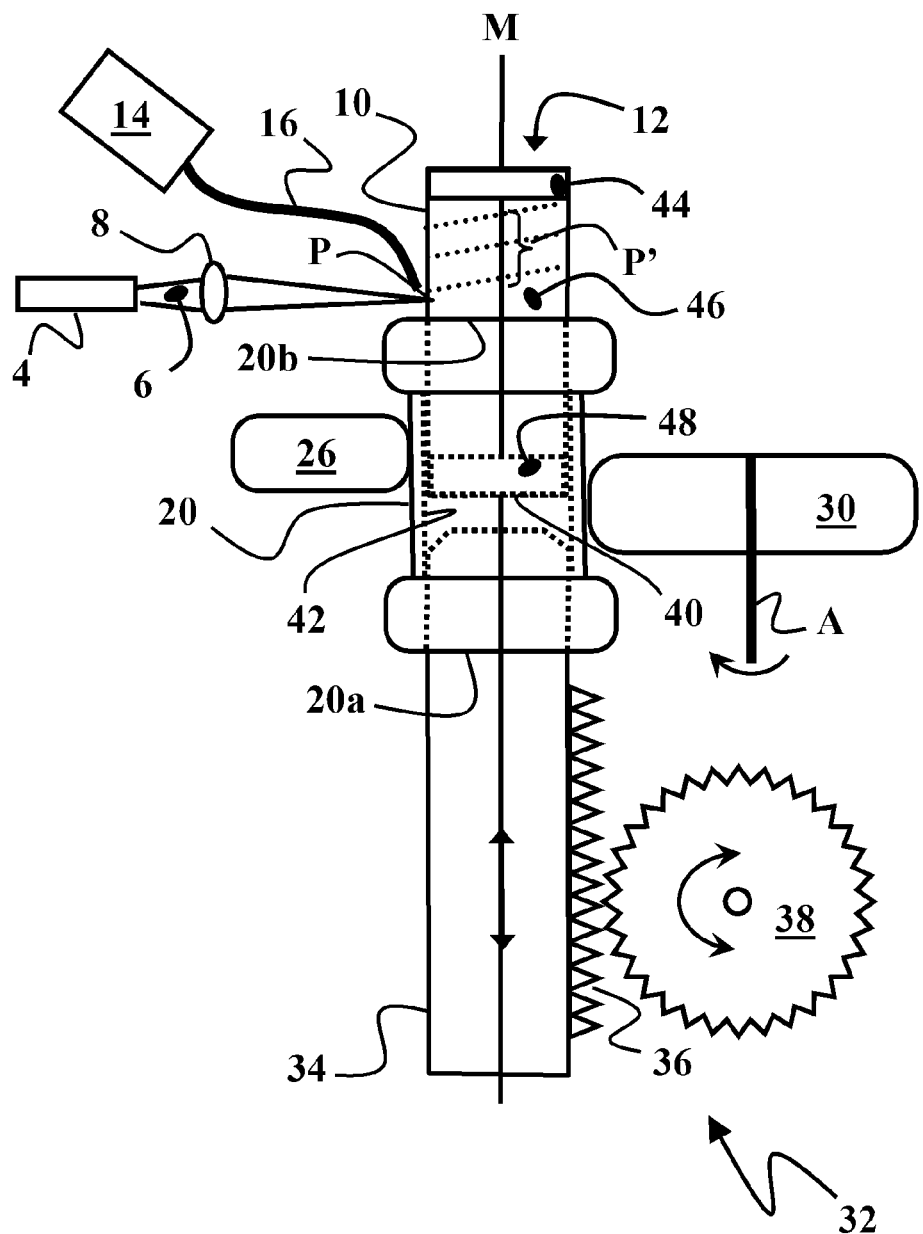

These and other advantages and features will be better understood from a consideration of the following description of one or more exemplary embodiments of the method and the system according to the present invention made with reference to the drawings of the accompanying figures, of which:

FIG. 1 Shows schematically an embodiment of a LIBS system according to the present invention; and FIG. 2 Shows schematically an embodiment of an actuator for use in a LIBS system according to the present invention.

Considering FIG. 1, an embodiment of a Laser Induced Breakdown Spectrocopy (LIBS) system 2 is illustrated (not to scale) as basically comprising a laser source 4 for emitting a pulsed laser beam 6 towards focussing optics 8 (here simply represented by lens) configured to focus the laser beam 6 onto an exposed portion of an outer surface 10 of a sample pellet 12 of a consolidated granular material, made for example by press-forming the granular material into a consolidated mass. In other embodiments an optical fiber may be employed to couple the laser beam 6 onto the exposed portion of outer surface 10 and focussing optics may be incorporated with the optical fiber. An optical spectrometer 14 is provided and is configured to perform spectral analysis of optical radiation emitted by a plasma produced by the focussed pulsed laser beam 6 on the exposed portion of the outer surface 10 of sample pellet 12 and to generate in a conventional manner LIBS spectral data therefrom. An optical fiber 16 is provided, in the present embodiment and by way of example only, to couple the optical radiation emitted by the plasma into the optical spectrometer 14.

The LIBS system 2 further comprises a sample station 18 configured to hold a tubular sample container 20 containing the sample pellet 12 of consolidated granular material and to present its outer peripheral surface 10 at a distance from the focussing optics 8, at which distance the laser beam 6 is focussed onto the so presented outer surface 10. The sample station 18 here comprises an open ended cylindrical housing 22 with an inner cylindrical surface 24. A set of rollers, here three, 26,28,30 are provided to hold the sample container 20 within the cylindrical housing 22. The sample station 18 also includes a rotary drive configured to impart rotational motion to the container 20 (hence to the exposed outer surface 10 of the sample pellet 12). This rotary motion has the advantage that multiple new portions of the outer surface 10 may be relatively simply presented for LIBS analysis. In the present embodiment at least one of the rollers, here roller 30, is driven to rotate, for example using a rotary motor mechanically coupled to an axle on which the roller 30 is mounted, and forms the rotary drive. At least one of the rollers, here roller 28, may be made to engage with and disengage from the container 20 to facilitate its insertion into and removal from the sample station 18. In the present embodiment the roller 28 is mounted at one end of a rocker arm assembly 29 and is biased away from the container using spring bias 31.

As illustrated in FIG. 2, an actuator 32 is configured to effect relative movement of the sample container 20 and the sample pellet 12 so as to slide the sample pellet 12 along a movement axis 'M' and gradually present different portions (P, P') of the outer surface 10 for exposure to the focussed, pulsed laser beam 6. In the present embodiment the actuator 32 comprises, for example, a piston 34 having a toothed lower portion 36 which engages with teeth of a rotatable cog wheel 38 so that when the cog wheel 38 rotates the piston 34 moves linearly along the movement axis M to contact with an end 40 of the sample pellet 12. Linear movement is thereby transferred to the sample pellet 12. In this manner the pellet 12 is slid out of the sample container 20 which is held stationary as the piston 34 moves through the sample container 20.

Initially, the outer surface 10 is in contact with and constrained by an inner surface 42 of the sample container 20 and expansion or relaxation of the outer surface 10 is prevented. Moreover, dust or other contamination cannot accumulate on the outer surface 10. This advantageously enables samples to be stored, for example during transportation from remote collection sites, without the sample surface to be exposed to the laser beam during the LIBS analysis relaxing to cause height variations or becoming contaminated.

Usefully the sample container 20 is a cylindrical tubular container which is open at both ends 20a, 20b. This facilitates the coupling of the movement of the piston 34 to the sample pellet 12 as the piston 34 can directly contact the pellet 12. Furthermore, with this construction the position of the outer surface 12 of the pellet 12 is maintained relative to the focal point of the laser beam as the container 20 rotates. In some embodiments the sample container 20 may be have different cross-sectional shapes or one end may be formed of a slidable end wall configured to slide along the inner surface 42 of sample container 20 without falling outside of the scope of the invention as claimed.

In use, the actuator 32 operates to present a portion P of the outer surface 10 of the sample pellet 12 at the focal point of the focussing optics 8. The laser 4 produces a pulsed laser beam 6, typically with an energy of less than 1 mJ and preferably between 0.1 mJ and 0.5 mJ at a repetition rate of greater than 100 Hz, which is focussed at the portion P of the outer surface 10 to cause breakdown of that portion P of the outer surface 10 and thereby generating a plasma containing optical radiation. The optical radiation is collected by optical fiber 16 and coupled into the spectrometer 14 for spectral analysis. The actuator 32 and the motorised roller 30 rotary drive are operated in concert to present for LIBS analysis a new portion of the outer surface 10 to the focussed laser beam 6 after one or more laser beam pulses. Thus, a spiral track (illustrated by points P') is traced by the laser beam 6 over the outer surface 10 of the sample pellet 12 during the analysis and collection of multiple instances of LIBS spectral data from the same sample is thereby facilitated.

By way of example, the LIBS system is configured to operate to provide the sample pellet 12 with three 'virtual' zones. A first zone 44 comprises a portion of the outer surface 10 first presented external of the sample container 20. No analysis is made from this first zone 44 and it is provided to limit the effects on the LIBS measurements of carry over between samples due to residue in the sample press used to form the sample pellets 12. A second zone 46 follows this first zone 44 and represents the portion of the outer surface 10 from which analysis is made and which is exposed to the pulsed laser beam 6 for LIBS analysis. A third zone 48 follows the second zone 46 and represents a holding portion of the sample pellet 12 which remains internal of the sample container 20 throughout the analysis.

A sample pellet 12 may be formed from a granular sample material through pelletizing the sample in a manner known in the art of LIBS analysis. Typically, the sample container 20 is located in the pellet press with its open ends along a vertical axis. A die is placed co-axially with and on top of the container 20. Sample is placed in the die and a ram, typically a pneumatic ram, applies several tons to consolidate the sample material and a sample pellet 12 of consolidated granular material is formed in the sample container 20.

In some applications the system may, as is known in the art, include a source of inert gas, such as Argon, for supply to the region at which laser ablation will be performed. This is to provide an inert atmosphere in which the plasma will be formed. In some applications the system may, as is known in the art, include a source of gas, such as compressed air, for cleaning optics of the system in order to remove debris that may collect there.

The invention claimed is:

1. A Laser Induced Breakdown Spectroscopy (LIBS) system, comprising:
    a laser source configured to emit a pulsed laser beam;
    a cylindrical tubular container configured to retain a sample pellet of a consolidated granular material, the cylindrical tubular container having opposing, first and second open ends; and
    a sample station configured to hold the cylindrical tubular container in one or more orientations to present an exposed surface of the sample pellet towards the pulsed laser beam, the sample station including
        an actuator including a piston that is configured to extend through the first open end of the cylindrical tubular container, the piston moveable along a movement axis between the first and second open ends to induce linear movement of the sample pellet along the movement axis and at least partially out of the cylindrical tubular container through the second open end to expose a portion of an outer side surface of the sample pellet previously constrained through contact with an inner surface of the cylindrical tubular container, and
        a rotary drive configured to induce a rotational motion of the cylindrical tubular container around the movement axis to rotate the outer side surface of the sample pellet around the movement axis to present the portion of the outer side surface as the exposed surface,
    wherein the sample station is configured to operate the actuator and the rotary drive in concert to simultaneously induce rotational motion of the outer side surface of the sample pellet around the movement axis and linear motion of the sample pellet along the movement axis through the second open end to present the exposed surface as a spiral pattern of portions of the outer side surface of the sample pellet, the spiral pattern extending around the movement axis.

2. The LIBS system of claim 1 wherein the laser is configured to emit a sequence of laser beam pulses at a repetition rate of greater than 100 Hz, each pulse of the sequence of laser beam pulses having an energy between 0.1mJ and 0.5 mJ.

3. A method of performing Laser Induced Breakdown Spectroscopy (LIBS) analysis of a sample pellet of a consolidated granular material comprising:
    positioning the sample pellet at a particular position and orientation, such that a portion of an outer side surface of the sample pellet is presented as an exposed surface at a particular distance from focusing optics of a LIBS system; and
    directing a sequence of laser beam pulses from a laser source onto the exposed surface of the sample pellet,
    wherein the positioning the sample pellet includes
        providing a cylindrical tubular container at a sample station, the cylindrical tubular container having opposing, first and second open ends, the cylindrical tubular container containing the sample pellet within an interior of the cylindrical tubular container between the first and second open ends, such that the outer side surface of the sample pellet is in contact with an inner surface of the tubular container, and
        inducing linear movement of the sample pellet along a movement axis out of the cylindrical tubular container through the second open end to expose a portion of the outer side surface previously constrained by the inner surface of the tubular container, and
        inducing rotational movement of cylindrical tubular container around the movement axis to rotate the outer side surface of the sample pellet around the movement axis to present the portion of the outer side surface as the exposed surface,
    wherein the inducing linear movement of the sample pellet along the movement axis out of the tubular container and the inducing rotational movement to the cylindrical tubular container around the movement axis are performed in concert to present the exposed surface as a spiral pattern of portions of the outer side surface of the sample pellet, the spiral pattern extending around the movement axis.

4. The method of claim 3, wherein the inducing linear movement of the sample pellet moves sequential portions of the outer surface out of the tubular container as the exposed surface, such that separate laser beam pulses of the sequence of laser beam pulses are directed onto separate, respective sequential portions of the outer surface.

* * * * *